(12) United States Patent
Behrens et al.

(10) Patent No.: US 8,084,507 B2
(45) Date of Patent: Dec. 27, 2011

(54) COSMETIC O/W EMULSION COMPRISING 1,2-HEXANEDIOL

(75) Inventors: Svea Behrens, Hamburg (DE); Andreas Bleckmann, Ahrensburg (DE); Rainer Kroepke, Schenefeld (DE); Uta Meiring, Hamburg (DE); Jens Nielsen, Henstedt-Ulzburg (DE)

(73) Assignee: Beiersdorf AG, Hamburg (DE)

( * ) Notice: Subject to any disclaimer, the term of this patent is extended or adjusted under 35 U.S.C. 154(b) by 637 days.

(21) Appl. No.: 11/585,244

(22) Filed: Oct. 24, 2006

(65) Prior Publication Data

US 2007/0092542 A1 Apr. 26, 2007

(30) Foreign Application Priority Data

Oct. 25, 2005 (DE) .......................... 10 2005 051 864

(51) Int. Cl.
*B01F 3/08* (2006.01)
*A61K 8/34* (2006.01)

(52) U.S. Cl. .............................. 516/53; 516/72; 424/405

(58) Field of Classification Search .................... 516/53; 424/405

See application file for complete search history.

(56) References Cited

U.S. PATENT DOCUMENTS

| | | | |
|---|---|---|---|
| 5,877,145 A | 3/1999 | Wahl et al. | |
| 6,274,124 B1 * | 8/2001 | Vollhardt | 424/59 |
| 7,582,681 B2 | 9/2009 | Schmaus et al. | |
| 2004/0191280 A1 * | 9/2004 | Nakajima et al. | 424/401 |
| 2004/0228888 A1 | 11/2004 | Kohlhase et al. | 424/401 |
| 2004/0258654 A1 * | 12/2004 | Nielsen et al. | 424/70.31 |
| 2005/0058679 A1 | 3/2005 | Kropke et al. | |
| 2005/0222276 A1 * | 10/2005 | Schmaus et al. | 514/738 |
| 2005/0238605 A1 * | 10/2005 | Kohlhase et al. | 424/70.13 |
| 2007/0041916 A1 | 2/2007 | Kropke et al. | |
| 2007/0054967 A1 * | 3/2007 | Schmaus et al. | 514/717 |
| 2007/0059331 A1 * | 3/2007 | Schmaus et al. | 424/405 |
| 2007/0265352 A1 | 11/2007 | Roeding et al. | |
| 2008/0268077 A1 * | 10/2008 | Vielhaber | 424/756 |

FOREIGN PATENT DOCUMENTS

| | | | |
|---|---|---|---|
| DE | 19915837 | | 10/2000 |
| DE | 10205190 | | 8/2003 |
| DE | 10341179 | | 3/2005 |
| DE | EP1559416 | * | 8/2005 |
| EP | 1078638 | | 2/2001 |
| EP | 1 426 029 A1 | | 1/2003 |
| WO | 91/07943 | | 6/1991 |
| WO | 95/01151 | | 1/1995 |
| WO | 98/53035 | | 11/1998 |
| WO | 03/699994 A1 | | 8/2003 |
| WO | 2004/050045 A1 | | 6/2004 |
| WO | 2006/045743 A1 | | 5/2006 |
| WO | 2006/082151 A2 | | 8/2006 |

OTHER PUBLICATIONS

"Cosmetic wipes to drive marker", Decisionnewsmedia, Mar. 30, 2004.*
Ingredients list of Regenerist Micro-Derm Cleansing Cloths.*
El-Mahrab-Robert et al. ("Assessment of oil polarity: Comparison of evaluation methods", International Journal of Pharmaceutics 348 (2008) 89-94).*
English language Abstract of DE 19915837, Oct. 12, 2000.
U.S. Appl. No. 11/585,217 (Behrens et al.), filed Oct. 24, 2006 and entitled "Emulsion Comprising 1,2-Alkanediols and Polar Oil Components".
U.S. Appl. No. 11/585,246 (Bleckmann et al.), filed Oct. 24, 2006 and entitled "Cosmetic Preparation with 1,2-Alkanediol and Triazines".
English language Abstract of DE 10341179, Mar. 13, 2005.
English language Abstract of DE 10205190, Aug. 21, 2003.

* cited by examiner

*Primary Examiner* — Ling Choi
*Assistant Examiner* — Chun-Cheng Wang
(74) *Attorney, Agent, or Firm* — Greenblum & Bernstein, P.L.C.

(57) ABSTRACT

A cosmetic oil-in-water emulsion which comprises 1,2-hexanediol and a method of preparing same.

25 Claims, No Drawings

COSMETIC O/W EMULSION COMPRISING 1,2-HEXANEDIOL

CROSS-REFERENCE TO RELATED APPLICATIONS

The present application claims priority under 35 U.S.C. §119 of German Patent Application No. 10 2005 051 864.8, filed Oct. 25, 2005, the disclosure of which is expressly incorporated by reference herein in its entirety.

BACKGROUND OF THE INVENTION

1. Field of the Invention

The present invention relates to a cosmetic preparation comprising 1,2-hexanediol.

2. Discussion of Background Information

The desire to appear beautiful and attractive is naturally rooted in man. Even if the beauty ideal has undergone changes over the course of time, the desire for a flawless outward appearance has always been the aim of human beings. The condition and the appearance of the skin is a significant part of a beautiful and attractive outward appearance.

In order for the skin to completely fulfill its biological functions it requires regular cleansing and care. Cleansing the skin thereby serves to remove dirt, perspiration and remains of dead skin particles which form an ideal breeding ground for pathogens and parasites of all types. Skin care products serve mostly to moisturize and regrease the skin. Active ingredients are often added to them which regenerate the skin and, for example, are intended to prevent and reduce its premature ageing (e.g., the appearance of fine lines and wrinkles).

Skin care products are usually composed of emulsions. Emulsions are generally understood as meaning heterogeneous systems which consist of two liquids which are immiscible or of only limited miscibility and which are usually referred to as phases and in which one of the two liquids is dispersed in the form of very fine droplets in the other liquid. Outwardly and viewed with the naked eye, emulsions appear homogeneous.

If the two liquids are water and oil and oil droplets are present in finely dispersed form in water, this is an oil-in-water emulsion (O/W emulsion, e.g., milk). The basic character of an O/W emulsion is defined by the water. In the case of a water-in-oil emulsion (W/O emulsion, e.g., butter), the principle is reversed, the basic character here being determined by the oil.

In order to keep emulsions stable over a prolonged period and to prevent separation of the phases, so-called emulsifiers are added to the emulsions. Emulsifiers as a rule are molecules with a polar, hydrophilic structural element and a nonpolar, lipophilic structural element. In the late 1940s a system was developed that was designed to facilitate the selection of emulsifiers. Each emulsifier was assigned a so-called HLB value (a dimensionless number between 0 and 20) that states whether a preferred water-solubility or oil-solubility is present. Numbers below 9 characterize oil-soluble, hydrophobic emulsifiers, numbers over 10, those that are water-soluble, hydrophilic.

In the production of an emulsion, the aqueous phase is combined with the lipid phase (oil phase) while being stirred, whereby the droplets of the internal phase of the emulsion have to be reduced to below 10 μm in size so that the emulsion becomes stable.

In the production of O/W emulsions with hydrophilic emulsifiers (emulsifiers with an HLB value of greater than/equal to 10) the problem often occurs that with the use of primarily moderately polar to polar lipids in the oil phase (i.e., lipids with a interfacial tension toward water of less than about 30 mN/m) an undesirable inversion of phases can occur. Furthermore, O/W emulsions of this type have a tendency towards phase inversion during storage, i.e., the preparations are often not very stable during storage.

It would be advantageous to have available an O/W emulsion with hydrophilic emulsifiers and a method for producing an O/W emulsion with hydrophilic emulsifiers with a substantially reduced phase inversion tendency during production and/or storage.

SUMMARY OF THE INVENTION

The present invention provides a cosmetic oil-in-water emulsion which comprises 1,2-hexanediol.

In one aspect, the emulsion may comprise from about 0.3% to about 3 % by weight, e.g., from about 0.5% to about 1.5% by weight of 1,2-hexanediol, based on a total weight of the emulsion.

In another aspect, the emulsion may further comprise one or more oil-in-water emulsifiers in a total concentration of from about 1.5 to about 6% by weight, e.g., from about 2 to about 4% by weight, based on a total weight of the emulsion. For example, the one or more oil-in-water emulsifiers may comprise one or more of glyceryl stearate citrate, polyglyceryl methyl glucose distearate and polyethylene glycol(2000) monostearate.

In yet another aspect, the emulsion of the present invention may further comprises one or more of phenoxyethanol, methylparaben and propylparaben and/or it may comprise tocopheryl acetate and/or it may comprise glycerol.

The present invention also provides a cosmetic oil-in-water emulsion which comprises from about 0.3% to about 3% by weight of 1,2-hexanediol and one or more oil-in-water emulsifiers in a total concentration of from about 1.5 to about 6% by weight, each based on a total weight of the emulsion.

In one aspect, this emulsion may comprise from about 0.5% to about 1.5% by weight of 1,2-hexanediol and/or may comprise the one or more oil-in-water emulsifiers in a total concentration of from about 2 to about 4% by weight.

In another aspect, the one or more oil-in-water emulsifiers may comprise one or more of glyceryl stearate citrate, polyglyceryl methyl glucose distearate and polyethylene glycol (2000) monostearate.

In yet another aspect, the emulsion may further comprises tocopheryl acetate and/or glycerol.

The present invention also provides an ointment, a cream or a lotion which comprises an emulsion of the present invention as set forth above, including the various aspects thereof.

The present invention also provides a method for producing a cosmetic oil-in-water emulsion. The method comprises (i) the addition of 1,2-hexanediol to the aqueous phase of the emulsion prior to heating and/or (ii) the addition of 1,2-hexanediol after heating during the cooling process to the developing emulsion at a temperature of from about 30° C. to about 40° C., e.g., at about 35° C.

In one aspect, the method may be carried out at a temperature of not higher than about 85° C.

The present invention also provides a cosmetic oil-in-water emulsion which is produced by the above process.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

The use of 1,2-hexanediol in cosmetic emulsions is known to one skilled in the art per se, but the prior art has not been able to shown the way to the present invention.

WO 95/01151 discloses the use of alkanediols having 5-7 carbon atoms in cosmetic preparations. However, O/W emulsions with 1,2-hexanediol are not explicitly disclosed. No exemplary embodiments with 1,2-hexanediol and/or with the emulsifiers according to the invention are disclosed, either.

DE 103 41 179 discloses deodorant compositions with a combination of alkane-1,2-diols and α- and/or β-hydroxy acids. However, O/W emulsions with 1,2-hexanediol and the emulsifiers according to the invention are not disclosed.

DE 102 05 190 discloses cosmetic preparations with a combination of polyols and one or more diols, including hexanediol. However, this document does not disclose any 1,2-hexanediol in an O/W emulsion.

EP 1 078 638 discloses sunscreen preparations with high concentrations of 1,2-hexanediol.

It is advantageous according to the present invention if hydrophilic emulsifiers with an HLB value of greater than/equal to about 10 are used as O/W emulsifiers. The HLB value of emulsifiers can be taken from the customary standard works (e.g., Fiedler, Lexikon der Hilfsstoffe für Pharmazie, Kosmetik und angrenzende Gebiete, Editio Cantor Verlag, Aulendorf).

It further is preferred according to the present invention if the O/W emulsifiers comprise one or more of glyceryl stearate citrate (CAS 39175-72-9, INCI glyceryl stearate citrate, e.g., Imwitor 370 from Hüls), polyglyceryl methyl glycose distearate (INCI polyglyceryl methyl glycose distearate, e.g., Tego Care 450 from Goldschmidt) and/or polyethylene glycol(2000) monostearate (INCI PEG40 stearate).

It also is preferred for the emulsion according to the present invention to be free from sodium dihydroxycetyl phosphate (e.g., Dragophos S).

Advantageously, the emulsion according to the present invention comprises tocopheryl acetate. Preferably, the emulsion comprises tocopheryl acetate in a concentration of from about 0.1% to about 1% by weight, more preferably in a concentration of from about 0.3% to about 0.7% by weight, based on the total weight of the preparation.

It further is advantageous for the emulsion according to the present invention to comprise phenoxyethanol, methylparaben and/or propylparaben. Preferably, these compounds are comprised in the emulsion in an individual concentration of from about 0.1% to about 1% by weight and more preferably in an individual concentration of from about 0.3% to about 0.7% by weight, based on the total weight of the preparation.

The emulsion according to the invention may, for example, have the consistency of an ointment, a cream or a low-viscosity lotion.

It also is preferred for the method according to the present invention to be carried out in the form of a hot-hot method. In this method a hot oil phase and a hot aqueous phase are combined with one another.

According to the invention it is particularly preferred if the method is carried out at a temperature of not higher than about 85° C.

According to the present invention the emulsion will advantageously be present as an ointment, a cream or a lotion (possibly sprayable).

The emulsion according to the present invention may, for example, also be used as a spray or an impregnation medium for a bandage or a wipe. Bandages and wipes impregnated with the emulsion according to the present invention are therefore also within the scope of the present invention.

The aqueous phase of the emulsion according to the present invention may advantageously comprise one or more customary cosmetic auxiliaries, such as, for example, alcohols, in particular those of low carbon number, preferably ethanol and/or isopropanol, diols or polyols of low carbon number, and ethers thereof, preferably propylene glycol, glycerol, butylene glycol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, self-tanning agents, insect repellents and in particular one or more thickeners, which may advantageously be chosen from silicon dioxide, aluminum silicates, polysaccharides and derivatives thereof, e.g. hyaluronic acid, xanthan gum, hydroxypropylmethylcellulose, particularly advantageously from polyacrylates, preferably a polyacrylate from the group of the so-called carbopols, for example, carbopol grades 980, 981, 1382, 2984, 5984, in each case individually or in combination.

The oil phase of the emulsion of the present invention may comprise, e.g., all the conventional constituents of oil, fat and wax components used in cosmetics. Also, the emulsion according to the present invention may advantageously comprise one or more cosmetic active ingredients and treatment substances, e.g., UV sunscreen filters. Preferably, corresponding active ingredients are contained in the preparation of the present invention in a total concentration of from about 0.01% to 30% by weight, based on the total weight of the preparation.

Further advantageous substances for incorporation in the preparation of the present invention include in particular, niacinamide, panthenol, aloe vera, hamamelis extract, polidocanol, vitamin E, vitamin A, vitamin A derivatives, vitamin C, vitamin C derivatives, coenzyme Q10, creatine, creatinine, taurine, alpha-glucosylrutin. These substances will usually be used in a total concentration of from about 0.1% to about 30% by weight, based on the total weight of the preparation.

Particularly preferably the preparation of the present invention comprises one or more alpha-hydroxy acids and/or salts thereof as further constituents. Lactic acid/lactate and/or citric acid/citrate are preferred and are preferably used in a concentration of from about 0.01% to about 5% by weight, based on the total weight of the preparation.

The preparation according to the present invention may also comprise other ingredients such as, e.g., perfumes in any desired concentration and quantity.

Unless stated otherwise, the numbers in the following Examples refer to % by weight.

EXAMPLES

| | Example | | | | | | | |
|---|---|---|---|---|---|---|---|---|
| | 1 | 2 | 3 | 4 | 5 | 6 | 7 | 8 |
| Glyceryl stearate citrate | | 1.0 | | 2.0 | | | | 2.0 |
| PEG-40 stearate | 1.0 | | | | | 1.5 | | |
| Polyglyceryl methyl glucose distearate | | | 2.0 | | 3.0 | | 1.5 | 0.5 |
| Glyceryl stearate | 1.5 | | | | | 1.5 | | |
| Cetyl alcohol | | 0.5 | | 2.0 | 1.5 | 0.75 | 1.0 | |
| Stearyl alcohol | | 0.5 | 0.5 | | | 0.75 | | |
| Cetearyl alcohol | 2.0 | | | | | | | 1.5 |
| Caprylic/capric triglyceride | 5.0 | 4.0 | | 5.0 | | 6.0 | 3.0 | 0.5 |
| Ethylhexyl cocoate | | | 2.0 | | | | 1.0 | |
| Octyldodecanol | | 1.0 | 3.0 | | 5.0 | | 2.0 | |
| Mineral oil | | | | 2.0 | | | | |
| Hydrogenated polyisobutene | 1.0 | | | | | | | |
| Polydecene | | | | 2.0 | | | | |
| Cyclomethicone | 2.0 | | | | | 3.0 | | |
| Dimethicone | 1.0 | | | | | | | 1.5 |
| Phenyltrimethicone | | | | | | 1.0 | | |
| Dicaprylyl carbonate | | 2.0 | | | 2.0 | | | 3.5 |
| Natural oils (such as, e.g., jojoba oil/sunflower oil | 1.5 | | 3.0 | 0.5 | 1.0 | | 2.0 | 2.5 |
| 1,2-Hexanediol | 0.5 | 0.75 | 2.0 | 0.3 | 1.0 | 1.2 | 0.5 | 0.75 |
| Trisodium EDTA | 0.2 | 0.1 | | 0.05 | | 0.1 | 0.3 | |
| Iminodisuccinate | 0.1 | | 0.1 | | 0.3 | | | 0.5 |
| Phenoxyethanol | 0.3 | 0.1 | | 0.5 | 0.7 | | | 0.4 |
| Parabens | 0.4 | | 0.3 | | 0.3 | | 0.2 | |
| Hexamidine diisethionate | | 0.1 | | | 0.05 | | 0.1 | |
| Imidodiazolidinyl urea | | | | | | 0.2 | | 0.2 |
| DMDM hydantoin | | | 0.2 | | | 0.1 | | |
| Iodopropynyl butylcarbamate | | | | 0.2 | | | 0.05 | |
| Glycerin | 10.0 | 3.0 | 7.0 | 8.0 | 15.0 | 20.0 | 0.5 | 2.0 |
| Tocopheryl acetate | 0.2 | 0.5 | 0.75 | | | 0.3 | | 1.0 |
| Alcohol denat. | 5.0 | | 2.5 | | | 7.5 | | 7.5 |
| Water | ad 100 | ad 100 | ad 100 | ad 100 | ad 100 | ad 100 | ad 100 | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic oil-in-water emulsion, wherein the emulsion comprises a total of from 1.0% to 3.0% by weight of one or more oil-in-water emulsifiers selected from glyceryl stearate citrate, polyglyceryl methyl glucose distearate, and PEG-40 stearate, and further comprises from 0.3% to 3% by weight of 1,2-hexanediol, based on a total weight of the emulsion.

2. The emulsion of claim 1, wherein the emulsion comprises at least about 0.5% by weight of 1,2-hexanediol.

3. The emulsion of claim 1, wherein the emulsion comprises not more than about 1.5% by weight of 1,2-hexanediol.

4. The emulsion of claim 1, wherein the emulsion comprises one or more oil-in-water emulsifiers in a total concentration of from about 1.5% to about 6% by weight, based on a total weight of the emulsion.

5. The emulsion of claim 1, wherein the emulsion comprises one or more oil-in-water emulsifiers in a total concentration of from about 2% to about 4% by weight.

6. The emulsion of claim 1, wherein the emulsion comprises glyceryl stearate citrate.

7. The emulsion of claim 1, wherein the emulsion comprises polyglyceryl methyl glucose distearate.

8. The emulsion of claim 1, wherein the emulsion comprises PEG-40 stearate.

9. The emulsion of claim 1, wherein the emulsion further comprises one or more of phenoxyethanol, methylparaben and propylparaben.

10. The emulsion of claim 1, wherein the emulsion further comprises tocopheryl acetate.

11. The emulsion of claim 1, wherein the emulsion further comprises one or more substances selected from alpha-hydroxy acids and salts thereof.

12. The emulsion of claim 11, wherein the one or more alpha-hydroxy acids and salts thereof comprise at least one of lactic acid/lactate and citric acid/citrate.

13. The emulsion of claim 1, wherein the emulsion is free of sodium dihydroxycetyl phosphate.

14. A cosmetic oil-in-water emulsion, wherein the emulsion comprises PEG-40 stearate and from 0.3% to 3% by weight of 1,2-hexanediol, based on a total weight of the emulsion.

15. The emulsion of claim 14, wherein the emulsion comprises at least about 0.5% by weight of 1,2-hexanediol.

16. The emulsion of claim 14, wherein the emulsion comprises not more than about 1.5% by weight of 1,2-hexanediol.

17. The emulsion of claim 14, wherein the emulsion comprises one or more oil-in-water emulsifiers which include PEG-40 stearate in a total concentration of from about 1.5% to about 6% by weight, based on a total weight of the emulsion.

18. The emulsion of claim 17, wherein the emulsion comprises the one or more oil-in-water emulsifiers in a total concentration of from about 2% to about 4% by weight.

19. The emulsion of claim 14, wherein the emulsion further comprises tocopheryl acetate.

20. A cosmetic oil-in-water emulsion, wherein the emulsion comprises one or more oil-in-water emulsifiers which comprise at least one of glyceryl stearate citrate, polyglyceryl methyl glucose distearate, and PEG-40 stearate, and further comprises from 0.3% to 3% by weight of 1,2-hexanediol, based on a total weight of the emulsion, and wherein 1,2-hexanediol is the only diol that is present in the emulsion.

21. The emulsion of claim 20, wherein the emulsion comprises at least about 0.5% by weight of 1,2-hexanediol.

22. The emulsion of claim 20, wherein the emulsion comprises not more than about 1.5% by weight of 1,2-hexanediol.

23. The emulsion of claim 20, wherein the emulsion comprises the one or more oil-in-water emulsifiers in a total concentration of from about 1.5% to about 6% by weight, based on a total weight of the emulsion.

24. The emulsion of claim 20, wherein the emulsion comprises the one or more oil-in-water emulsifiers in a total concentration of from about 2% to about 4% by weight.

25. The emulsion of claim 20, wherein the emulsion further comprises tocopheryl acetate.

\* \* \* \* \*